US012005225B2

(12) United States Patent
Corato et al.

(10) Patent No.: US 12,005,225 B2
(45) Date of Patent: *Jun. 11, 2024

(54) LINE MANAGEMENT DEVICE

(71) Applicant: JMC Global Technologies I, L.P., Roanoke, TX (US)

(72) Inventors: Craig Douglas Corato, Roanoke, TX (US); Janalee Marie Corato, Roanoke, TX (US); Huy Phuong Nguyen, San Mateo, CA (US)

(73) Assignee: JMC GLOBAL TECHNOLOGIES I, L.P., Roanoke, TX (US)

( * ) Notice: Subject to any disclaimer, the term of this patent is extended or adjusted under 35 U.S.C. 154(b) by 1124 days.

This patent is subject to a terminal disclaimer.

(21) Appl. No.: 16/809,691

(22) Filed: Mar. 5, 2020

(65) Prior Publication Data

US 2020/0197602 A1    Jun. 25, 2020

Related U.S. Application Data

(63) Continuation-in-part of application No. 13/458,635, filed on Apr. 27, 2012, now Pat. No. 10,583,242.

(60) Provisional application No. 61/480,172, filed on Apr. 28, 2011.

(51) Int. Cl.
  *A61M 5/14*    (2006.01)
  *F16B 2/08*    (2006.01)
(52) U.S. Cl.
  CPC ............. *A61M 5/1418* (2013.01); *F16B 2/08* (2013.01)
(58) Field of Classification Search
  CPC ........ A61M 5/1418; A61M 2205/0216; A61M 2205/60; A61M 2205/6009; F16B 2/08

USPC ....................... 248/49, 51, 52, 74.3; 604/179
See application file for complete search history.

(56) References Cited

U.S. PATENT DOCUMENTS

| | | | |
|---|---|---|---|
| 1,782,404 A | | 11/1930 | Howly et al. |
| 2,449,882 A | * | 9/1948 | Daniels ................. A61M 25/02 604/179 |
| 3,059,645 A | | 10/1962 | Hasbrouck et al. |
| 3,082,984 A | * | 3/1963 | Larsson .................... F16L 3/13 174/72 A |
| 3,471,109 A | * | 10/1969 | Meyer .................... F16L 3/2332 248/68.1 |
| 3,659,319 A | * | 5/1972 | Erickson ................. H02G 3/266 24/304 |
| 4,088,136 A | | 5/1978 | Hasslinger et al. |
| 4,316,461 A | * | 2/1982 | Marais .................. A61M 5/425 604/179 |
| 4,480,639 A | | 11/1984 | Peterson et al. |

(Continued)

*Primary Examiner* — Kimberly T Wood
(74) *Attorney, Agent, or Firm* — Edwin S. Flores; Daniel J. Chalker; Chalker Flores, LLP

(57) ABSTRACT

The present invention includes a line management device for attaching to a fixture wherein the line management device simultaneously retains one or more patient care lines in an opening, wherein the device comprises: a flexible strap comprising a proximal strap end comprising a single slot positioned through a portion of the proximal strap end; a body portion connected to the proximal strap end, wherein the body portion comprises a channel positioned on top of the flexible strap that forms an opening through which the one or more patient care lines are positioned; and a distal strap end connected to the body portion, wherein the distal strap end extends through the single slot to secure the distal strap end to the proximal strap end.

16 Claims, 10 Drawing Sheets

(56) References Cited

U.S. PATENT DOCUMENTS

| | | | | |
|---|---|---|---|---|
| 4,585,443 A * | 4/1986 | Kaufman | | A61M 5/52 604/179 |
| 4,586,924 A * | 5/1986 | Lanning | | A61M 5/425 128/869 |
| 4,671,787 A | 6/1987 | Widman | | |
| 5,084,026 A | 1/1992 | Shapiro | | |
| 5,395,343 A | 3/1995 | Iscovich | | |
| 5,397,639 A | 3/1995 | Tollini | | |
| 5,876,371 A | 3/1999 | Yokoyama et al. | | |
| D424,692 S | 5/2000 | Monaghan et al. | | |
| 6,113,577 A * | 9/2000 | Hakky | | A61M 25/02 604/179 |
| 6,315,759 B1 | 11/2001 | Peterson | | |
| 6,395,343 B1 | 5/2002 | Strangman | | |
| 6,500,154 B1 | 12/2002 | Hakky et al. | | |
| 6,526,981 B1 * | 3/2003 | Rozier | | A61M 25/02 128/877 |
| 6,544,232 B1 | 4/2003 | McDaniel | | |
| 7,255,251 B1 * | 8/2007 | Smith | | A61B 5/15003 604/179 |
| D622,480 S | 8/2010 | Heitkamp | | |
| 7,766,289 B2 | 8/2010 | Newkirk et al. | | |
| D817,489 S | 5/2018 | Nelson et al. | | |
| 2005/0137496 A1 | 6/2005 | Walsh et al. | | |
| 2006/0064950 A1 | 3/2006 | Ford et al. | | |
| 2007/0282272 A1 * | 12/2007 | Bannon | | A61M 5/1418 604/174 |
| 2009/0105656 A1 | 4/2009 | Schaeffer | | |
| 2009/0281502 A1 | 11/2009 | Heitkamp | | |
| 2010/0301176 A1 * | 12/2010 | Werner | | F16L 3/26 248/65 |
| 2011/0011989 A1 * | 1/2011 | Samolej | | F16L 3/24 248/74.3 |
| 2012/0277682 A1 | 11/2012 | Corato et al. | | |
| 2013/0294018 A1 * | 11/2013 | Mochizuki | | F16L 3/06 361/679.01 |

* cited by examiner

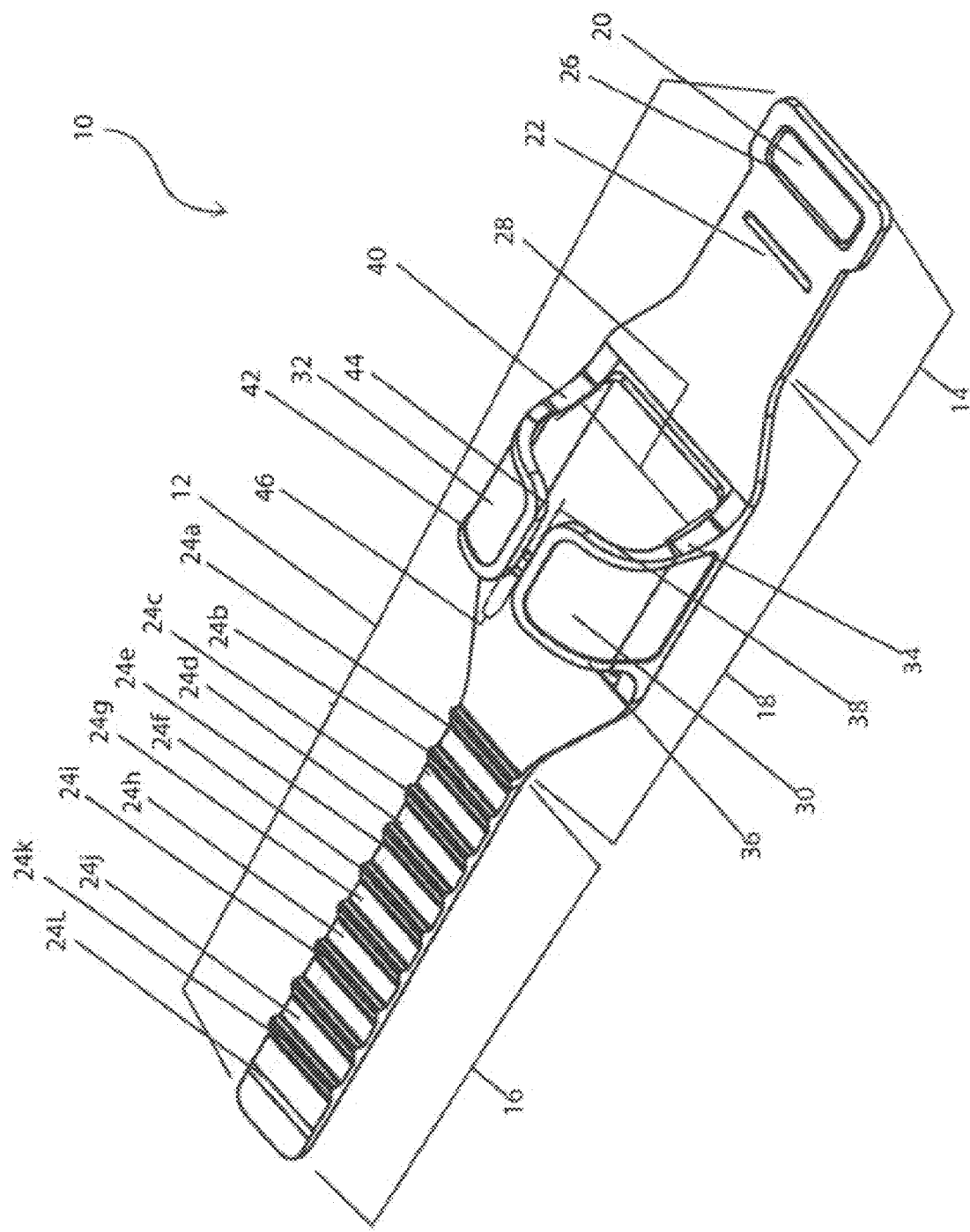

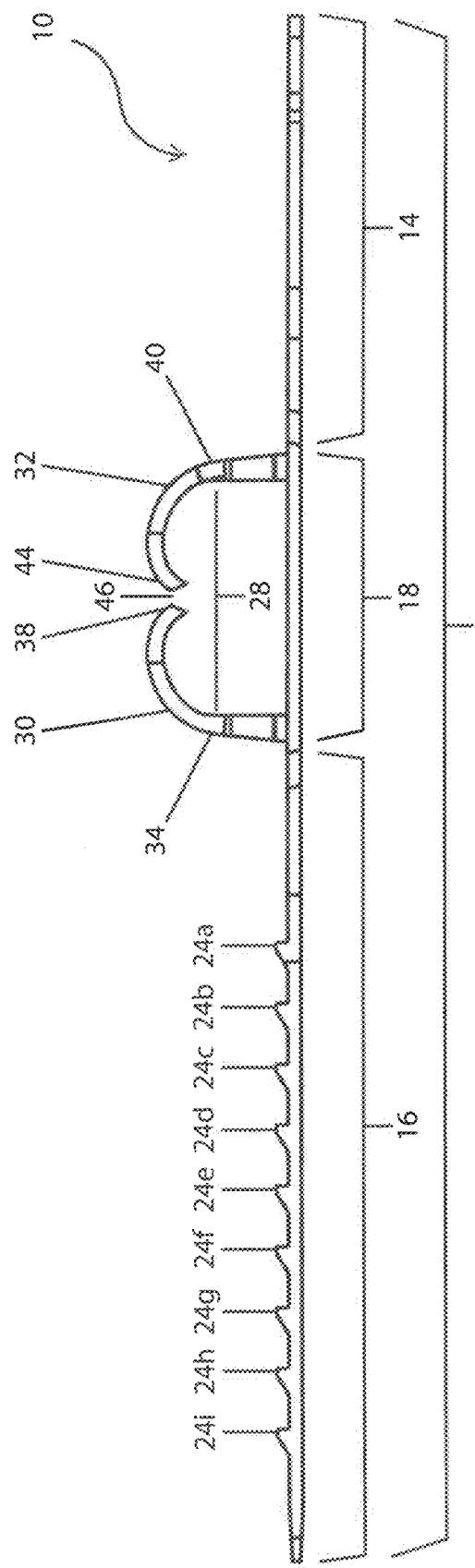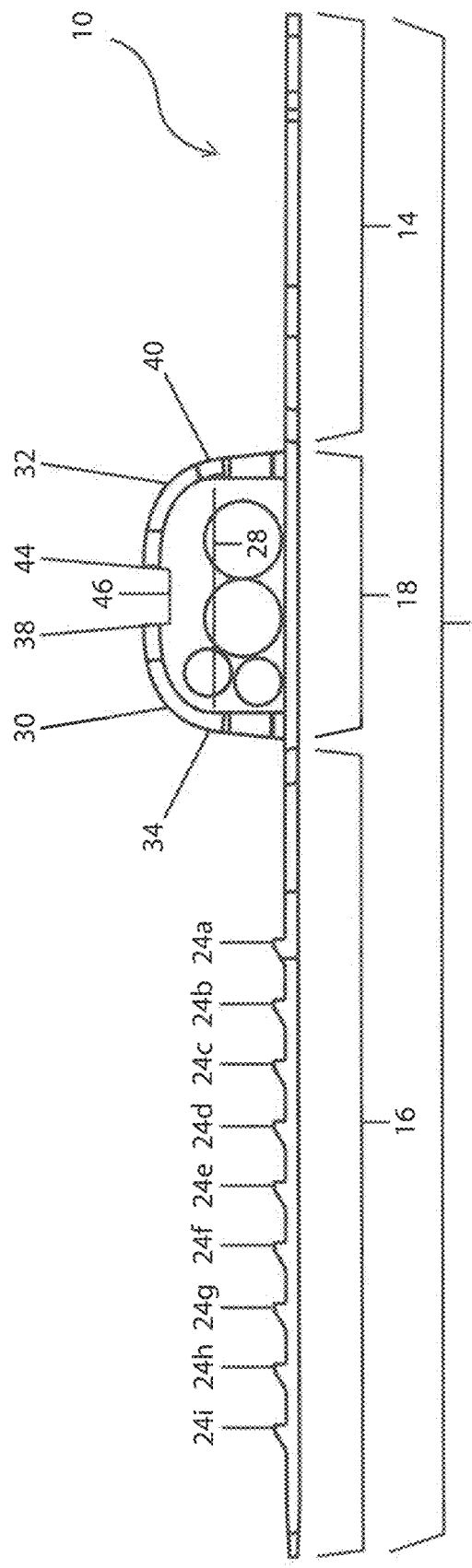
FIG. 6A
FIG. 7A

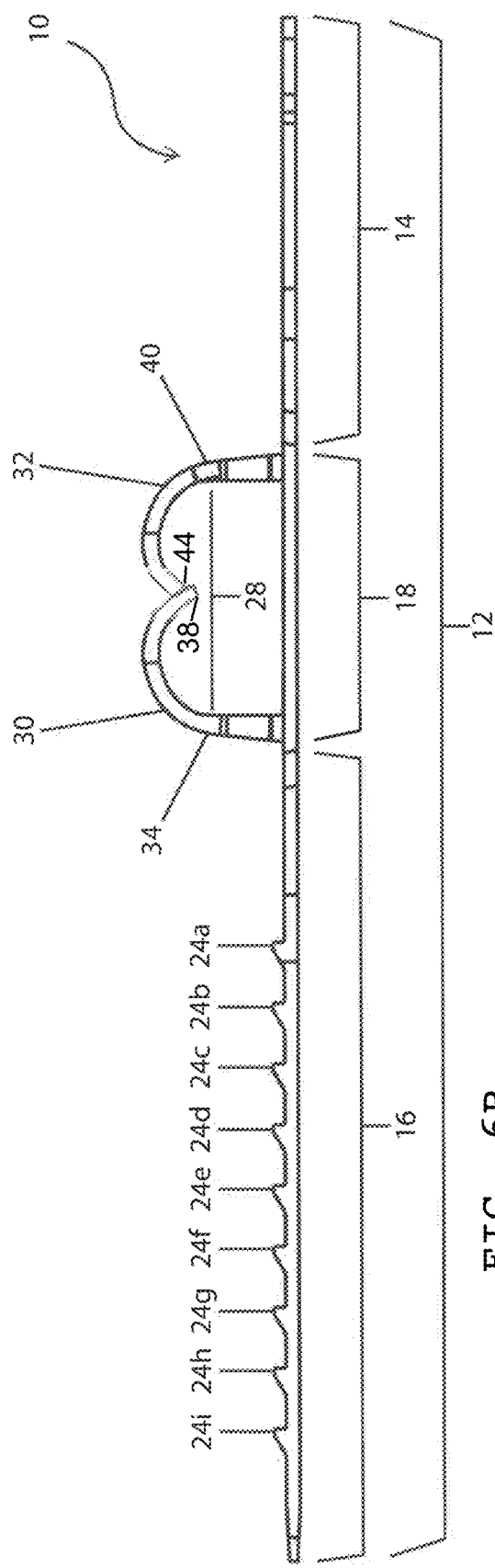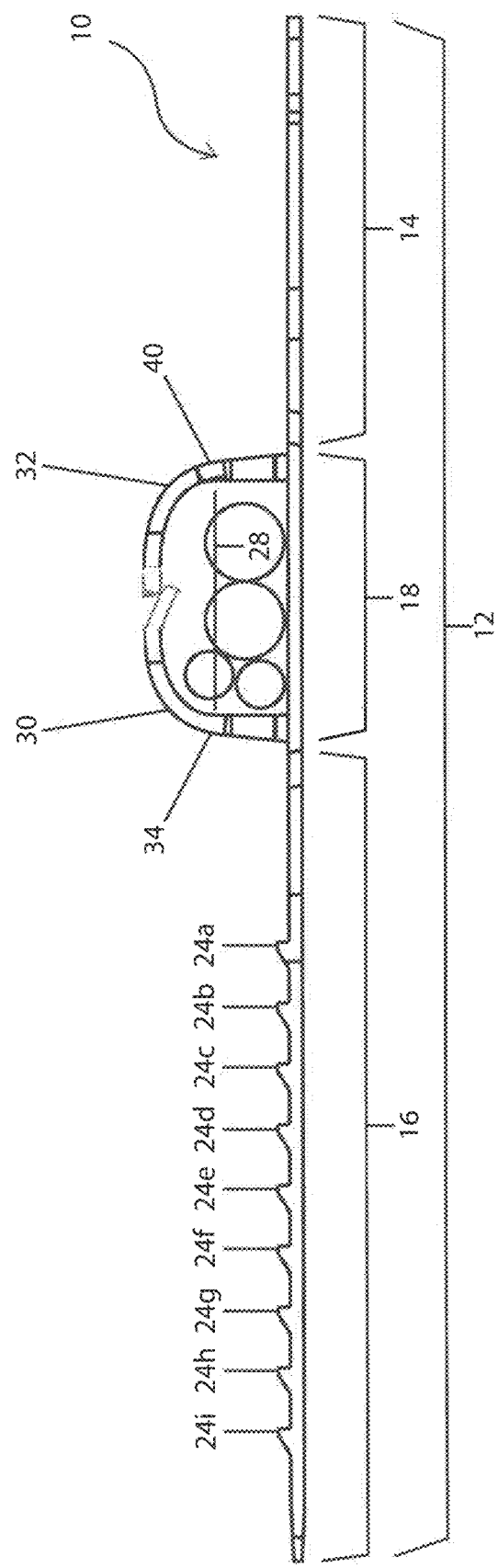

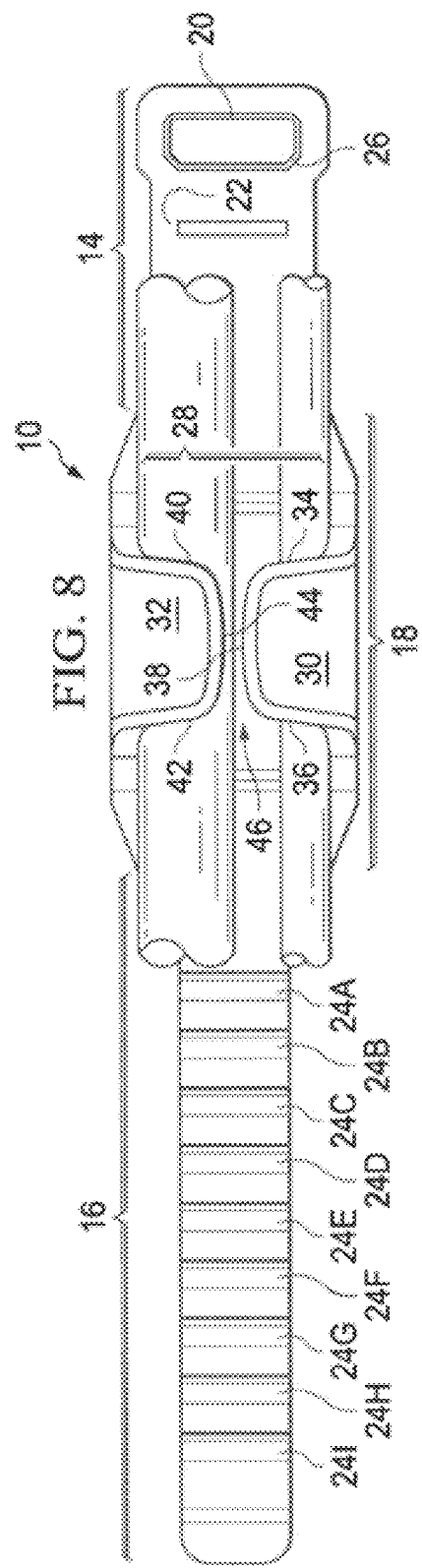

LINE MANAGEMENT DEVICE

CROSS-REFERENCE TO RELATED APPLICATIONS

This application is a continuation-in-part of U.S. patent application Ser. No. 13/458,635, filed Apr. 27, 2012, which claims priority to U.S. Provisional Patent Application Ser. No. 61/480,172, filed Apr. 28, 2011, the contents of which are incorporated by reference in their entirety.

TECHNICAL FIELD OF THE INVENTION

This invention relates generally to hospital appliances, and, more particularly, to a simple but effective line management device that may be used to organize and protect intravenous lines, and other types of tubing and electrical connections to bedridden patients.

STATEMENT OF FEDERALLY FUNDED RESEARCH

Not applicable.

INCORPORATION-BY-REFERENCE OF MATERIALS FILED ON COMPACT DISC

Not applicable.

BACKGROUND OF THE INVENTION

Without limiting the scope of the invention, its background is described in connection with a line management device to manage one or more care lines to a patient. Patients in hospitals, in home care, etc., often require patient care equipment (e.g., heart monitoring equipment, medical gas delivery equipment, infusion pumps, intravenous bags, equipment monitors, and defibrillators) to be in close proximity and often directly connected to the patient. These intravenous lines, cables, wires and tubes extend from the equipment to the patient and dangle or hang without intermediate support. Many of these lines are put into place or connected to the patient's body prior to the patient being transported. As such, the intravenous lines, cables, wires, and tubes are intertwined, displaced, or entangled, requiring careful tracing to determine the identity of each line, thereby compromising the ability of the attending caregivers to adequately treat the patient. Often these lines are secured to a patient support device, a floor, a wall, an equipment support, or other device by a fastener, tape, or other means to prevent unintentional movement of the lines or tubes to prevent tripping, accidental movement or snagging one of the lines.

For example, U.S. Pat. No. 7,766,289 discloses a patient line management device to manage one or more patient care lines. The line management device includes a line manager coupled to a support. The support is adapted to be coupled to a patient support.

For example, U.S. Pat. No. 6,315,759 entitled "Protective Cover for Intravenous Lines and Other Elongated Members," discloses a protective cover used to surround one or more elongated members such as a plurality of intravenous lines. The cover may be used to cover or protect baby crib rails, bicycle frame sections, handles, and other items wherein the cover assumes the form of a generally cylindrical hollow tube composed of a flexible, resilient material such as closed-cell foam. The tube includes a slit running lengthwise down the tube, enabling the tube to be placed around and over the elongated member by spreading the slit to expose a pair of adjacent, opposing surfaces, each with a length equal to the length of the tube and a width equal to the thickness of the wall. The tube preferably further includes means, other than the tube itself, for maintaining the tube in position around the member. In one configuration, the means for maintaining the tube in position around the member includes an adhesive on one or both of the opposing surfaces, which may be covered with a release layer to expose the adhesive. A separate release layer may be used to cover the slit as well. The means for maintaining the tube in position around the member may also include at least one elongated adhesive strip disposed on the inner wall of the tube. When used to cover and protect intravenous lines, the release layer covering the slit, or a portion of the outer wall covered by the release layer may include one or more messages concerning the use, or re-use of the cover.

For example, U.S. Pat. No. 5,876,371 entitled "Intravenous Tube Holder," discloses an intravenous tube holder for use in a trauma unit or similar environment which includes at least one element, each element preferably containing a plurality of tracks, each track being designed to secure a separate intravenous tube, said element further having a writing surface on the same side of the element as the tracks, with a writing surface next to each track for identifying the content and/or other dosage information identifying the contents of the intravenous tube therein. Each element further has a projection on the side opposite the tracks and writing surfaces for attaching the element to a support means. Each element has a male extension and female indent for interconnecting to additional elements so as to accommodate a greater number of intravenous tubes.

SUMMARY OF THE INVENTION

The present invention includes a line manager to hold and removably secure within an aperture one or more lines or tubes adjacent to a patient on or near a bed rail, or other device. In some embodiments, the line manager is attached to a bed rail of a hospital or medical bed, IV poles, any other structure in the room, or body part and may be used to position and label the various tubes or lines going to and from the patient. The line manager may be made of a flexible material and can be a single use device or a multiple use device.

In one embodiment, the present invention includes a line management device for attaching to a fixture that retains one or more patient care lines, wherein the device comprises: a flexible strap comprising a proximal strap end comprising a single slot positioned through a portion of the proximal strap end; a body portion connected to the proximal strap end, wherein the body portion comprises: a channel positioned on top of the flexible strap: wherein the channel is formed by (a) a bottom located under the one or more patient care lines, wherein the bottom is formed from the body portion, (b) a first curved flexible tab that extends from the body portion and curves towards (c) an adjacent second curved flexible tab that extends from the body portion and curves towards the first curved flexible tab, wherein the bottom and the first curved flexible tab and the adjacent second curved flexible tab form an opening that accommodates one or more patient care lines, wherein the opening is sized to allow the one or more patient care lines to be placed within the opening and the opening retains the one or more patient care lines without longitudinally restraining the one or more patient care lines or contacting the first curved flexible tab and the adjacent second curved flexible tab; and a distal strap end connected to the body portion, wherein the distal strap end extends through the single slot to secure the distal strap end to the proximal strap end. In one aspect, the flexible strap is rubber, polymer, plastic, or combinations thereof. In another aspect, the channel is parallel to the proximal strap end. In another aspect, the channel is perpendicular to the proximal strap end. In another aspect, the first curved flexible tab and the adjacent second curved tab flexible overlap. In another aspect, the opening does not restrain the one or more patient care lines.

In another embodiment, the present invention includes a line management device for removably simultaneously retaining one or more patient care lines comprising: a flexible strap comprising a proximal strap end that comprises a securing mechanism; a body portion connected to the proximal strap end, wherein the body portion comprises: a channel positioned on top of the flexible strap wherein the channel is formed by (a) a bottom located under the one or more patient care lines, wherein the bottom is formed from the body portion, (b) a first curved flexible tab that extends from the body portion and curves towards (c) an adjacent second curved flexible tab that extends from the body portion and curves towards the first curved flexible tab, wherein the first curved flexible tab and the adjacent second curved flexible tab overlap or form an opening wherein the opening is sized to allow the one or more patient care lines to be simultaneously placed within the opening and the opening simultaneously retains the one or more patient care lines without longitudinally restraining or contacting the first curved flexible tab and the adjacent second curved flexible tab the one or more patient care lines; and a distal strap end connected to the body portion, wherein the distal strap end comprises a connection mechanism that engages the securing mechanism of the proximal strap end to removably secure the proximal strap end to the distal strap end. In one aspect, the channel is parallel to the proximal strap end. In another aspect, the channel is perpendicular to the proximal strap end. In another aspect, the first curved tab and the adjacent second curved tab overlap. In another aspect, the securing mechanism comprises a hook closure and the connection mechanism comprises a loop closure to mate the securing mechanism and the connection mechanism. In another aspect, the securing mechanism and the connection mechanism comprise: a hook closure to mate the securing mechanism and the connection mechanism; a tab closure and the connection mechanism comprises an aperture closure to mate the securing mechanism and the connection mechanism; an aperture closure at the proximal strap end and the connection mechanism comprises a tab closure at the distal strap end to mate the securing mechanism and the connection mechanism; a single slot at the distal strap end and the connection mechanism comprises a tab at the proximal strap end, wherein the tab extends through the single slot to secure the securing mechanism and the connection mechanism; or a tab at the proximal strap end and the connection mechanism comprises a single slot at the distal strap end, wherein the tab extends through the single slot to secure the securing mechanism and the connection mechanism. In another aspect, the tab comprises one or more ridges to fit the securing mechanism and the connection mechanism.

In another embodiment, the present invention includes a method for retaining one or more patient care lines with a line management device comprising the steps of: providing a flexible strap comprising a proximal strap end comprising a single slot positioned through a portion of the proximal strap end that comprises: a body portion connected to the proximal strap end, wherein the body portion comprises: a channel positioned on top of the flexible strap, wherein the channel is formed by (a) a bottom located under the one or more patient care lines, wherein the bottom is formed from the body portion, (b) a first curved flexible tab that extends from the body portion and curves towards (c) an adjacent second curved flexible tab that extends from the body portion and curves towards the first curved flexible tab, wherein the bottom and the first curved flexible tab and the adjacent second curved flexible tab form an opening that accommodates one or more patient care lines, wherein the opening is sized to allow the one or more patient care lines to be placed within the opening and the opening retains, but does not longitudinally restraining or contacting the first curved flexible tab or the adjacent second curved flexible tab, or both, the one or more patient care lines; and a distal strap end connected to the body portion, wherein the distal strap end extends through the single slot to secure the distal strap end to the proximal strap end; and attaching the device to a fixture, wherein one or more patient care lines can be placed and removed from the opening. In one aspect, the flexible strap is rubber, polymer, plastic, or combinations thereof. In another aspect, the channel is parallel to the proximal strap end. In another aspect, the channel is perpendicular to the proximal strap end. In another aspect, the first curved tab and the adjacent second curved tab overlap. In another aspect, the opening does not restrain the one or more patient care lines.

The present invention provides flexible line management device for one or more patient care lines comprising: a flexible strap comprising a proximal end comprising one or more slots positioned through a portion of the proximal end; a body portion connected to the proximal end, wherein the body portion comprises a first curved tab that extends from the body portion and curves towards an adjacent second curved tab that extends from the body portion and curves towards the first curved tab; a channel formed between the first curved tab and the adjacent second curved tab; and a channel aperture formed between a first edge of the first curved tab adjacent a second edge of the adjacent second curved tab to allow access to the channel; a distal end connected to the body portion, wherein the distal end extends through the one or more slots to secure the distal end to the proximal end. One embodiment of the present invention includes a flexible line management device where the flexible strap is rubber and the channel may be parallel to the proximal end or perpendicular to the proximal end. Furthermore, in some embodiments, the first curved tab and the adjacent second curved tab overlap.

The present invention provides a line management device for one or more patient care lines comprising: a flexible strap comprising a proximal end comprises a securing mechanism; a body portion connected to the proximal end, wherein the body portion comprises a first curved tab that extends from the body portion and curves towards an adjacent second curved tab that extends from the body portion and curves towards the first curved tab; a channel formed between the first curved tab and the adjacent second curved tab; and a channel aperture formed between a first edge of the first curved tab adjacent a second edge of the adjacent second curved tab to allow access to the channel; a distal end connected to the body portion, wherein the distal end comprises a connection mechanism that engages the securing mechanism to removably secure the proximal end to the distal end.

One embodiment of the present invention includes a flexible line management device where the channel is parallel to the proximal end or perpendicular to the proximal end. The securing mechanism comprises a hook closure to the connection mechanism comprises a loop closure to mate the securing mechanism and the connection mechanism; a loop closure and the connection mechanism comprises a hook closure to mate the securing mechanism and the connection mechanism; a tab closure and the connection mechanism comprises an aperture closure to mate the securing mechanism and the connection mechanism; an aperture closure and the connection mechanism comprises a tab closure to mate the securing mechanism and the connection mechanism; one or more slots closure and the connection mechanism comprises a tab, wherein the tab extends through the one or more slots to secure the securing mechanism and the connection mechanism; a tab closure and the connection mechanism comprises one or more slots, wherein the tab extends through the one or more slots to secure the securing mechanism and the connection mechanism; the tab comprises one or more ridges to frictionally fit the securing mechanism and the connection mechanism.

The present invention provides a method of managing one or more cables or lines for a patient by providing a flexible line management device comprising a flexible strap comprising a proximal end comprising one or more slots positioned through a portion of the proximal end; a body portion connected to the proximal end, wherein the body portion comprises a first curved tab that extends from the body portion and curves towards an adjacent second curved tab that extends from the body portion and curves towards the first curved tab; a channel formed between the first curved tab and the adjacent second curved tab; and a channel aperture formed between a first edge of the first curved tab adjacent a second edge of the adjacent second curved tab to allow access to the channel; a distal end connected to the body portion; extending the flexible line management device around an object; connecting the distal end through the one or more slots to secure the distal end to the proximal end; and securing one or more cables or lines through the channel aperture into the channel. The object comprises a bed, bed rail support, a pole, a support, a cable, an arm, a leg or an IV stand.

In one embodiment, the present invention includes a line management device for attaching to a fixture wherein the device simultaneously retains two or more patient care lines, wherein the device comprises: a flexible strap comprising a proximal strap end comprising one or more slots positioned through a portion of the proximal strap end; a body portion connected to the proximal strap end, wherein the body portion comprises: a channel positioned on top of the flexible strap, wherein the channel is formed by (a) a bottom located under the one or more patient care lines, wherein the bottom is formed from the body portion, (b) a first curved flexible tab that extends from the body portion and curves towards (c) an adjacent second curved flexible tab that extends from the body portion and curves towards the first curved flexible tab, wherein the bottom and the first curved flexible tab and the adjacent second curved flexible tab form the channel; wherein the channel allows the one or more patient care lines to be placed within the channel and the channel simultaneously retains the two or more patient care lines without longitudinally restraining the one or more patient care lines between the first curved flexible tab, the adjacent second curved flexible tab and the bottom of the channel; and a distal strap end connected to the body portion, wherein the distal strap end extends through the one or more slots to secure the distal strap end to the proximal strap end. In one aspect, the flexible strap is an elastomeric material such as rubber. In another aspect, the channel is parallel to the proximal strap end. In another aspect, the channel is perpendicular to the proximal strap end. In another aspect, the first curved tab and the adjacent second curved tab overlap.

BRIEF DESCRIPTION OF THE DRAWINGS

For a more complete understanding of the features and advantages of the present invention, reference is now made to the detailed description of the invention along with the accompanying figures and in which:

FIG. 1A is a perspective view of one embodiment of the line manager of the present invention.

FIG. 6A is a side view of one embodiment of the line manager of the present invention.

FIG. 6B is a side view of another embodiment of the line manager of the present invention.

FIG. 7A is a side view of one embodiment of the line manager of the present invention in use.

FIG. 7B is a side view of another embodiment of the line manager of the present invention in use.

FIG. 8 is a top view of one embodiment of the line manager of the present invention in use.

DETAILED DESCRIPTION OF THE INVENTION

Figure 1B:
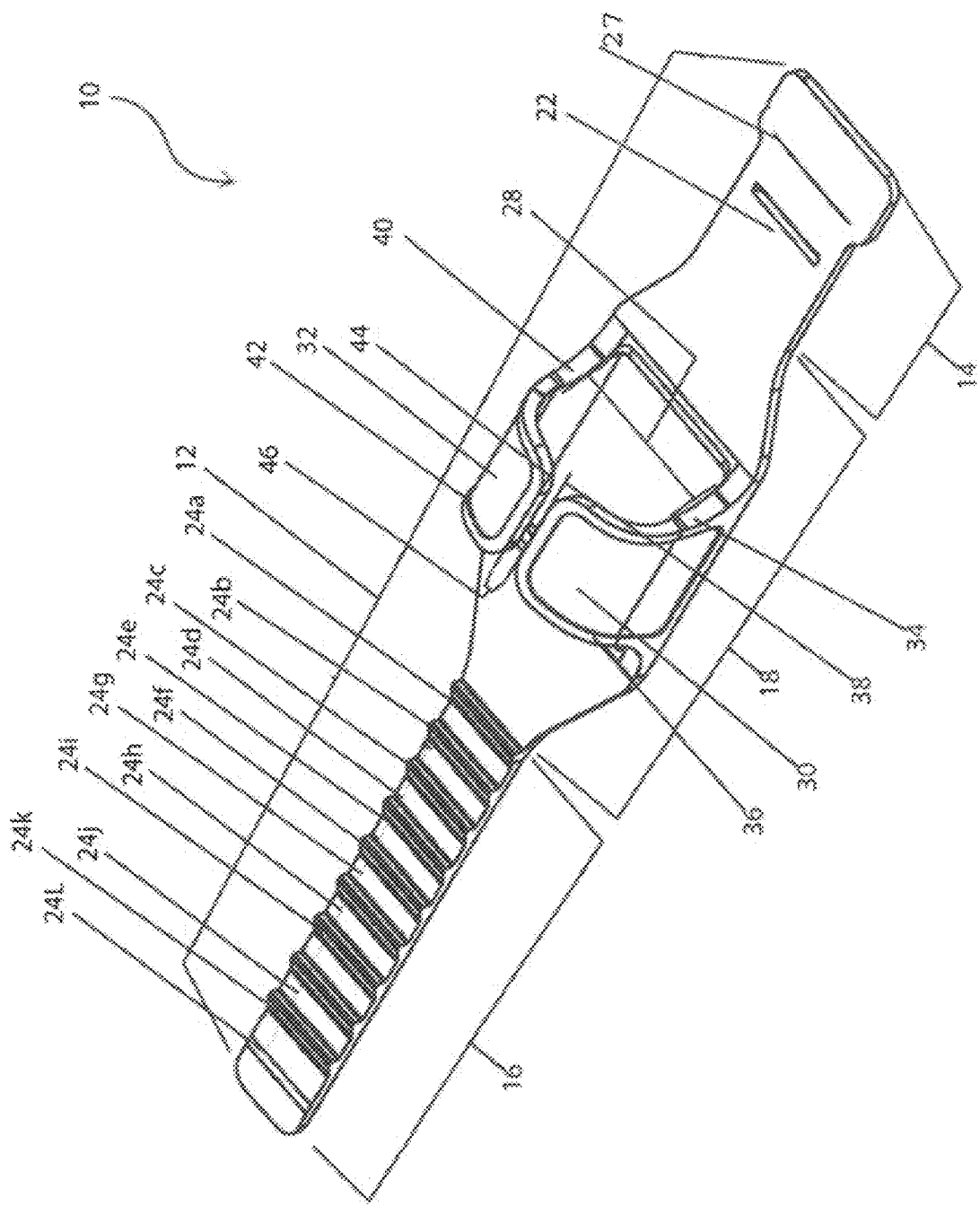
FIG. 1B is a perspective view of another embodiment of the line manager of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention includes a line manager to hold and removably secure within an aperture, one or more lines, or tubes adjacent to a patient, on or near a bed rail/rod, or other device. In some embodiments, the line manager is attached to a bed rail of a hospital, or medical bed and may be used to position and label the various tubes or lines going to the patient. The line manager may be made of a flexible material and can be a single use device or a multiple use device.

The present invention includes a line manager to hold and removably secure within an aperture one or more lines or tubes adjacent to a patient on or near a bed rail, or other device. In some embodiments, the line manager is attached to a bed rail of a hospital or medical bed, IV poles, any other structure in the room, or body part and may be used to position and label the various tubes or lines going to and from the patient. The line manager may be made of a flexible material and can be a single use device or a multiple use device.

The present invention includes a line manager made from a flexible material including but not limited to a flexible elastomeric material, such as, rubber, polymer, plastic, or combinations thereof. In addition, the present invention may be constructed as a single piece or in separate pieces and assembled. Advantages of the present invention include reduced cost, increased reliability, consistent repeatability in manufacturing, and durability with no additional parts to maintain. In addition, the present invention may use a substrate material and design (empty space on "ear flaps") to label or mark tubing using a marker (SHARPIE®, etc.) or colored embodiment to mark and label with the patient's name, type of fluid/tube used, nurse's name, doctor's name, etc. In addition, the present invention includes a retention feature (loop) designed into the strap to force the unused portion of the strap to be neatly oriented down and away from the user to keep the long strap from getting in the way of the doctors and nurses along with being a convenient one-handed (pull down motion) way of securing the present invention. The present invention includes a designed to "tear-away" upon removal to allow for quick-emergency removal. In addition, this ensures that a new sanitized band is utilized for each patient to avoid the spreading of bacteria, etc. The line manager can be made from different colors to permit the user to know different characteristics of the patient (e.g., fall risk, cardiovascular, needs to be helped to the restroom, etc.), or of the lines being used (e.g., delivering antibiotics, serum, plasma, whole blood, electrical impulse data, beat-beat or other monitoring, etc.), or both. As used herein, the phrases "patient treatment lines" or "patient care lines" refer to different electrical, fluid (gas or liquid), fiber-optic, etc., lines that can be attached to a patient during care or a treatment and that exit the area surrounding the patient to attach externally from a patient bed or other patient care are or environment. These patient care lines are otherwise traversing the patient care area in different directions and can be splayed out over different parts of the patient, they can tangle, roll under a patient, become entangled in bedding, and/or cover or traverse over an area of the patient undergoing treatment (thus eliminated the sterile field) or can become caught in wound dressings, or other parts of the patient, thus causing harm to the patient. The present invention gathers those lines into one or more line management devices that control the location of the line(s) on or about the patient, can be moved to different locations on the bed or other patient support structures, and can be disposable, that is, made sterile for single use.

FIG. 1A is a perspective view of one embodiment of the line manager 10 of the present invention. The line manager 10 is made of a flexible material to allow it to be secured to the bed rail such that the patient lines are positioned at, or above the patient and in some instances at, or above the top surface of the mattress. Alternatively, the line manager 10 may be attached to the patient directly or to a support located adjacent to the patient. The line manager 10 includes a strap 12 extending from a proximal end 14, and a distal end 16, separated by a body portion 18. The strap 12 is flexible and can be wrapped or positioned about a surface, body part, or rod. The proximal end 14 includes one or more slots 20 and 22. Although the embodiment in FIG. 1 depicts two slots 20 and 22, other embodiments may include 1, 2, 3, 4, 5, 6 etc., slots. In addition, the proximal end 14 may include a snap or a loop-and-hook fastener, or a combination thereof to secure the proximal end 14, and the distal end 16.

The distal end 16 extends to a length sufficient to encircle an object that is to be secured, and as such the length may vary between embodiments. The distal end 16 may optionally have one or more ridges 24a-24l extending from the surface of the distal end 16. The width of the distal end 16 is sized as to frictionally fit through the one or more slots 20 and 22. In embodiments with one or more ridges 24a-24l extending from the surface of the distal end 16, the one or more ridges 24a-24l contact the one or more slots 20 and 22 to frictionally secure the proximal end 14, and the distal end 16 about the object (not shown) to be secured. The distal end 16 may extend through the slot 20 and contact the divider 26 and further extend through the slot 22 such that the one or more ridges 24a-24l contact the divider 26 and secures the line manager 10. The body portion 18 includes a channel 28 formed by a first tab 30 and a second tab 32. The first tab 30 includes a first proximal edge 34 and a first distal edge 36 separated by a first edge 38. Adjacent the first tab 30 is a second tab 32 that includes a second proximal edge 40 and a second distal edge 42 separated by a second edge 44. A channel aperture 46 is formed between the first edge 38 and the second edge 44. In some instances, the first edge 38 and the second edge 44 are overlapped to further secure the channel 28.

FIG. 1B is a perspective view of another embodiment of the line manager 10 of the present invention. In FIG. 1B, line manager 10 has only the single slot 22, omitting slot 20 and divider 26. In line manager 10, slot 22 has an edge 27. In line manager 10 as depicted here, the width of the distal end 16 is sized so as to frictionally fit through the slot 22. In embodiments with one or more ridges 24a-24l extending from the surface of the distal end 16, the one or more ridges 24a-24l contact the slot 22 to frictionally secure the proximal end 14, and the distal end 16 about the object (not shown) to be secured. The distal end 16 extends through the slot 22 such that the one or more ridges 24a-24l contact the edge 27 and secures the line manager 10. The first edge 38 and the second edge 44 are overlapped to further secure the channel 28.

Figure 2:
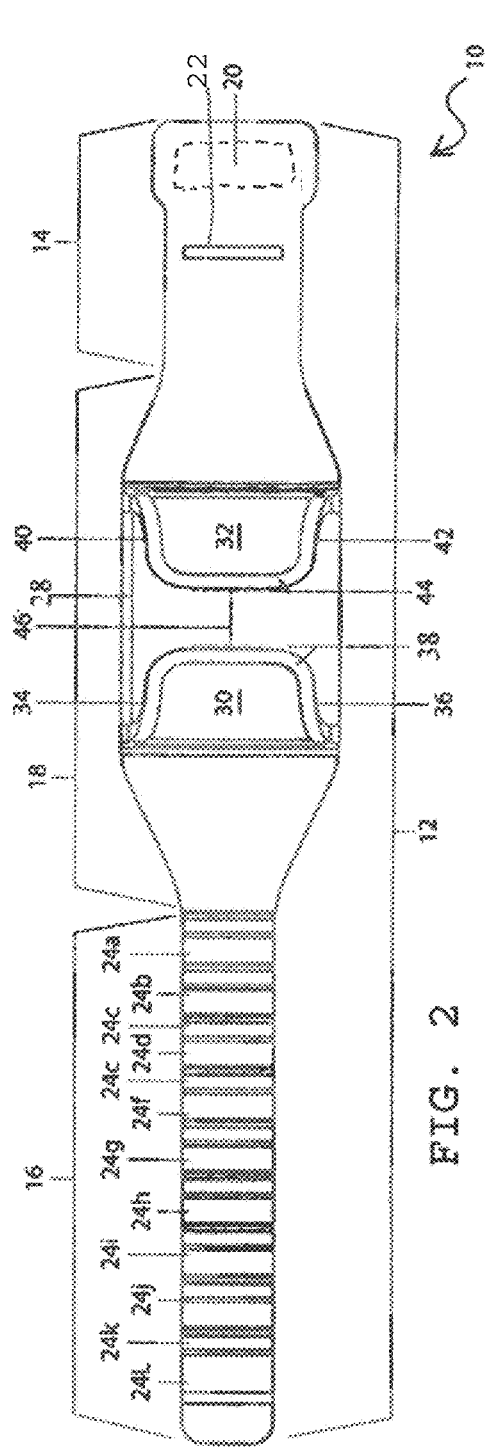
FIG. 2 is a top view of one embodiment of the line manager of the present invention.

FIG. 2 is a top view of one embodiment of the line manager 10 of the present invention. The line manager 10 is made of a flexible material to allow it to be secured to the bed rail such that the patient lines are positioned at, or above the patient, and in some instances at, or above the top surface of the mattress. The line manager 10 includes a strap 12 extending from a proximal end 14 and a distal end 16 separated by a body portion 18. The strap 12 is flexible and can be wrapped or positioned about a surface or rod (not shown). The proximal end 14 includes one or more slots although the embodiment in FIG. 2 depicts one optional slot 20 and a second slot 22, other embodiments may include 1, 2, 3, 4, 5, etc., slots. In addition, the proximal end 14 may include a snap (not shown) or a loop-and-hook fastener (not shown) or a combination thereof to secure the proximal end 14 and the distal end 16. The distal end 16 extends to a length sufficient to encircle an object that is to be secured, and as such, the length may vary between embodiments. The distal end 16 may optionally have one or more ridges 24a-24l extending from the surface of the distal end 16. The width of the distal end 16 is sized as to frictionally fit through the slot 20. In embodiments with one or more ridges 24a-24l extending from the surface of the distal end 16, the one or more ridges 24a-24l contact the slot 20 to frictionally secure the proximal end 14 and the distal end 16 about the object (not shown). The distal end 16 may extend through the slot 20 such that the one or more ridges 24a-24l contact the slot 20 to secures the line manager 10. The body portion 18 includes a channel 28 formed by a first tab 30 and a second tab 32. The first tab 30 includes a first proximal edge 34 and a first distal edge 36 separated by a first edge 38. Adjacent the first tab 30 is a second tab 32 that includes a second proximal edge 40 and a second distal edge 42 separated by a second edge 44. A channel aperture 46 is formed between the first edge 38 and the second edge 44. In some instances, the first edge 38 and the second edge 44 are overlapped to further secure the channel 28.

Figure 3:
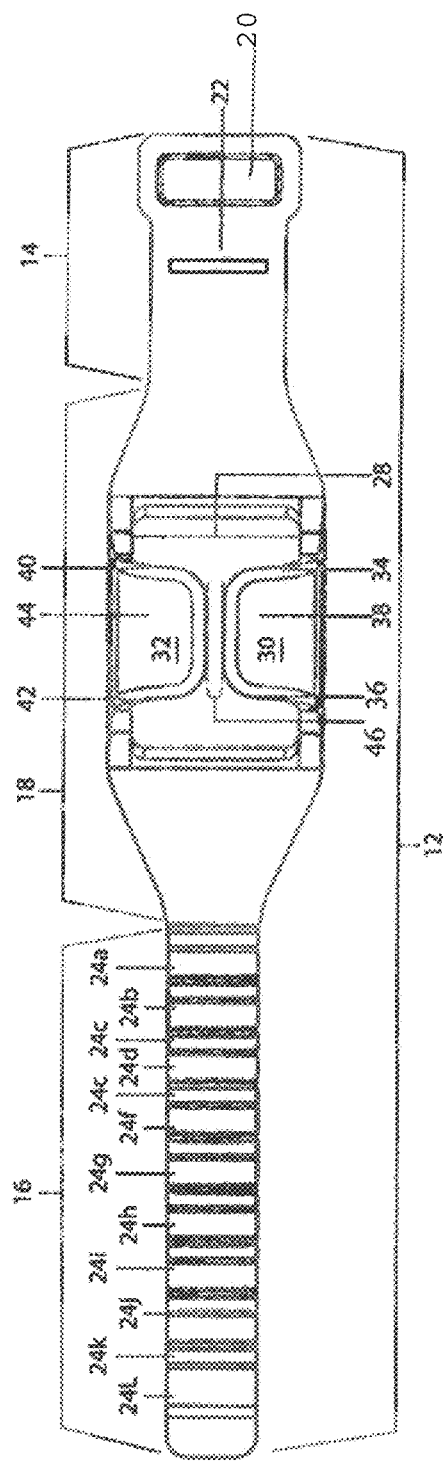
FIG. 3 is a top view of one embodiment of the line manager of the present invention.

FIG. 3 is a top view of one embodiment of the line manager 10 of the present invention. The line manager 10 is made of a flexible material to allow it to be secured to the bed rail such that the patient lines are positioned at or above the patient and in some instances at or above the top surface of the mattress. The line manager 10 includes a strap 12 extending from a proximal end 14 and a distal end 16 separated by a body portion 18. The strap 12 is flexible and can be wrapped or positioned about a surface or rod. The proximal end 14 includes one or more slots although the embodiment in FIG. 3 depicts a slot 20 and a slot 22, other embodiments may include 1, 2, 3, 4, 5, etc. slots. In addition, the proximal end 14 may include a snap (not shown) or a loop-and-hook fastener (not shown) or a combination thereof to secure the proximal end 14 and the distal end 16. The distal end 16 extends to a length sufficient to encircle an object that is to be secured, and as such, the length may vary between embodiments. The distal end 16 may optionally have one or more ridges 24a-24l extending from the surface of the distal end 16. The width of the distal end 16 is sized as to frictionally fit through the slot 22. In embodiments with one or more ridges 24a-24l extending from the surface of the distal end 16, the one or more ridges 24a-24l contact the slot 22 to frictionally secure the proximal end 14 and the distal end 16 about the object (not shown). The distal end 16 may extend through the slot 22 such that the one or more ridges 24a-24l contact the slot 22 to secure the line manager 10. The body portion 18 includes a channel 28 formed by a first tab 30 and a second tab 32. The first tab 30 includes a first proximal edge 34 and a first distal edge 36 separated by a first edge 38. Adjacent the first tab 30 is a second tab 32 that includes a second proximal edge 40 and a second distal edge 42 separated by a second edge 44. A channel aperture 46 is formed between the first edge 38 and the second edge 44. In some instances, the first edge 38 and the second edge 44 are overlapped to further secure the channel 28.

Figure 4:
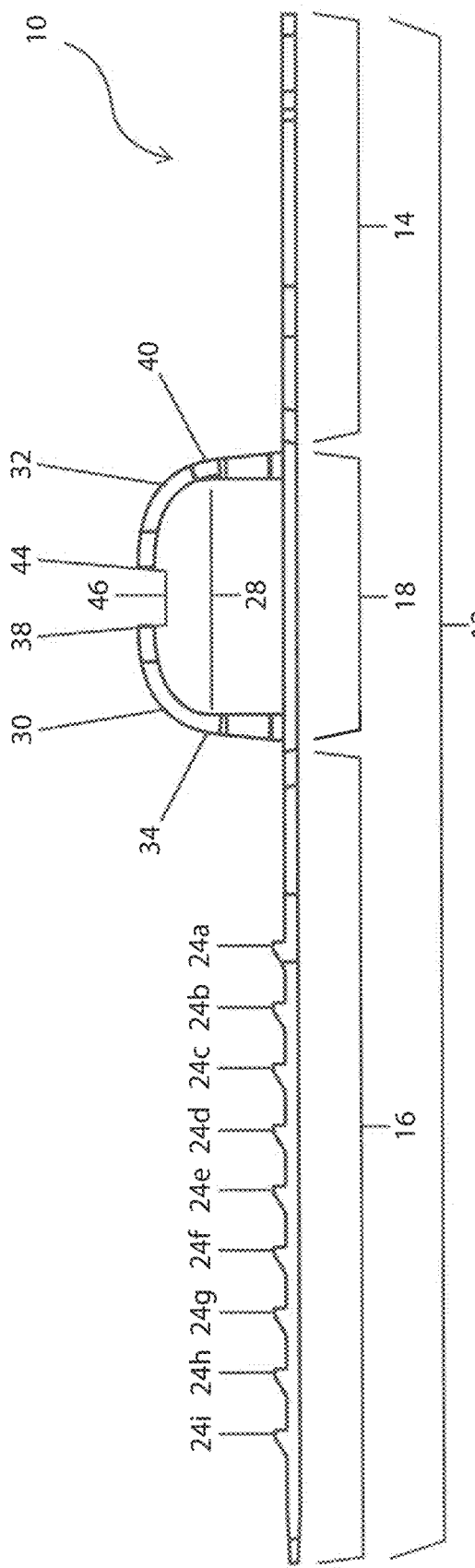
FIG. 4 is a side view of one embodiment of the line manager of the present invention.

FIG. 4 is a side view of one embodiment of the line manager 10 of the present invention. The line manager 10 is made of a flexible material to allow it to be secured to the bed rail such that the patient lines are positioned at or above the patient and in some instances at or above the top surface of the mattress. The line manager 10 includes a strap 12 extending from a proximal end 14 and a distal end 16 separated by a body portion 18. The strap 12 is flexible and can be wrapped or positioned about a surface or rod. The proximal end 14 includes one or more slots (not shown). In addition, the proximal end 14 may include a snap or a loop-and-hook fastener or a combination thereof to secure the proximal end 14 and the distal end 16. The distal end 16 extends to a length sufficient to encircle an object that is to be secured, and as such the length may vary between embodiments. The distal end 16 may optionally have one or more ridges 24a-24i extending from the surface of the distal end 16. The width of the distal end 16 is sized as to frictionally fit through the one or more slots (not shown). The distal end 16 may extend through the slot (not shown) and contact the divider (not shown) and further extend through the slot (not shown) such that the one or more ridges 24a-24i contact the divider (not shown) and secures the line manager 10. The body portion 18 includes a channel 28 formed by a first tab 30 and a second tab 32. The first tab 30 includes a first proximal edge 34 and a first distal edge (not shown) separated by a first edge 38. Adjacent the first tab 30 is a second tab 32 that includes a second proximal edge 40 and a second distal edge (not shown) separated by a second edge 44. A channel aperture 46 is formed between the first edge 38 and the second edge 44. In some instances, the first edge 38 and the second edge 44 are overlapped to further secure the channel 28.

Figure 5:
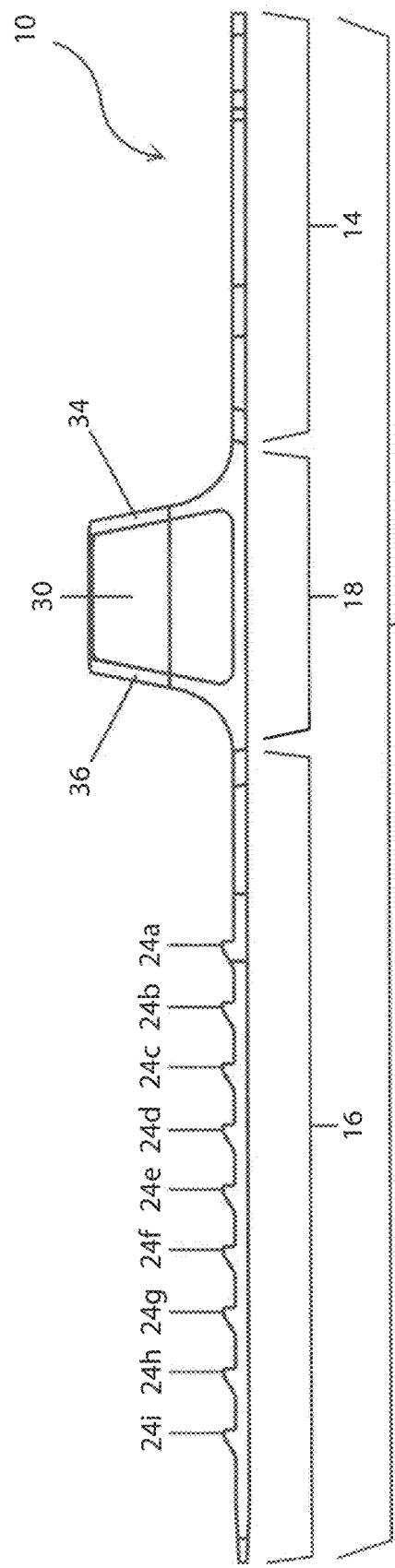
FIG. 5 is a side view of another embodiment of the line manager of the present invention.

FIG. 5 is a side view of another embodiment of the line manager 10 of the present invention. The line manager 10 is made of a flexible material to allow it to be secured to the bed rail such that the patient lines are positioned at or above the patient and in some instances at or above the top surface of the mattress. The line manager 10 includes a strap 12 extending from a proximal end 14 and a distal end 16 separated by a body portion 18. The strap 12 is flexible and can be wrapped or positioned about a surface or rod. The proximal end 14 includes one or more slots (not shown) although the embodiment in FIG. 1 depicts two slots (not shown), other embodiments may include 1, 2, 3, 4, 5, etc., slots. In addition, the proximal end 14 may include a snap (not shown) or a loop-and-hook fastener (not shown) or a combination thereof to secure the proximal end 14 and the distal end 16. The distal end 16 extends to a length sufficient to encircle an object that is to be secured, and as such the length may vary between embodiments. The distal end 16 may optionally have one or more ridges 24a-24i extending from the surface of the distal end 16. The width of the distal end 16 is sized as to frictionally fit through the one or more slots (not shown). In embodiments with one or more ridges 24a-24i extending from the surface of the distal end 16, the one or more ridges 24a-24i contact the one or more slots (not shown) to frictionally secure the proximal end 14 and the distal end 16 about the object (not shown). The distal end 16 may extend through the slot (not shown) and contact the divider (not shown) and further extend through the slot (not shown) such that the one or more ridges 24a-24i contact the divider (not shown) and secures the line manager 10. The body portion 18 includes a channel (not shown) formed by a first tab 30 and a second tab (not shown). The first tab 30 includes a first proximal edge 34 and a first distal edge 36 separated by a first edge (not shown). Adjacent the first tab 30 is a second tab (not shown) that includes a second proximal edge (not shown) and a second distal edge (not shown) separated by a second edge (not shown). A channel aperture (not shown) is formed between the first edge (not shown) and the second edge (not shown). In some instances, the first edge (not shown) and the second edge (not shown) are overlapped to further secure the channel (not shown).

FIG. 6A is a side view of one embodiment of the line manager 10 of the present invention. The line manager 10 is made of a flexible material to allow it to be secured to the bed rail such that the patient lines are positioned at or above the patient and in some instances at or above the top surface of the mattress. The line manager 10 includes a strap 12 extending from a proximal end 14 and a distal end 16 separated by a body portion 18. The strap 12 is flexible and can be wrapped or positioned about a surface or rod. The proximal end 14 includes one or more slots (not shown). In addition, the proximal end 14 may include a snap or a loop-and-hook fastener or a combination thereof to secure the proximal end 14 and the distal end 16. The distal end 16 extends to a length sufficient to encircle an object that is to be secured, and as such the length may vary between embodiments. The distal end 16 may optionally have one or more ridges 24a-24i extending from the surface of the distal end 16. The width of the distal end 16 is sized as to frictionally fit through the one or more slots (not shown). The distal end 16 may extend through the slot (not shown) and contact the divider (not shown) and further extend through the slot (not shown) such that the one or more ridges 24a-24i contact the divider (not shown) and secures the line manager 10. The body portion 18 includes a channel 28 formed by a first tab 30 and a second tab 32. The first tab 30 includes a first proximal edge 34 and a first distal edge (not shown) separated by a first edge 38. Adjacent the first tab 30 is a second tab 32 that includes a second proximal edge 40 and a second distal edge (not shown) separated by a second edge 44. A channel aperture 46 is formed between the first edge 38 and the second edge 44. In some embodiments, as shown in FIG. 6B, the first edge 38 and the second edge 44 are overlapped to further secure the channel 28.

FIG. 7A is a side view of one embodiment of the line manager 10 of the present invention in use. The line manager 10 is made of a flexible material to allow it to be secured to the bed rail such that the patient lines are positioned at or above the patient and in some instances at or above the top surface of the mattress. The line manager 10 includes a strap 12 extending from a proximal end 14 and a distal end 16 separated by a body portion 18. The strap 12 is flexible and can be wrapped or positioned about a surface or rod. The proximal end 14 includes one or more slots (not shown). In addition, the proximal end 14 may include a snap or a loop-and-hook fastener or a combination thereof to secure the proximal end 14 and the distal end 16. The distal end 16 extends to a length sufficient to encircle an object that is to be secured, and as such the length may vary between embodiments. The distal end 16 may optionally have one or more ridges 24a-24i extending from the surface of the distal end 16. The width of the distal end 16 is sized as to frictionally fit through the one or more slots (not shown). The distal end 16 may extend through the slot (not shown) and contact the divider (not shown) and further extend through the slot (not shown) such that the one or more ridges 24a-24i contact the divider (not shown) and secures the line manager 10. The body portion 18 includes a channel 28 formed by a first tab 30 and a second tab 32. The first tab 30 includes a first proximal edge 34 and a first distal edge (not shown) separated by a first edge 38. Adjacent the first tab 30 is a second tab 32 that includes a second proximal edge 40 and a second distal edge (not shown) separated by a second edge 44. A channel aperture 46 is formed between the first edge 38 and the second edge 44. In some instances, the first edge 38 and the second edge 44 are overlapped to further secure the channel 28. In this figure, four patient lines are depicted simultaneously positioned within the channel 28, which patient lines are retained without longitudinally restraining one or more patient care lines between the first curved flexible tab, the adjacent second curved flexible tab and the bottom of the channel. In other words, the patient lines are able to slide along the longitudinal axis of the patient line, but are removably restrained within the channel. Thus, the patient line is capable of being moved along its longitudinal axis to accommodate a repositioning of the patient line, e.g., when a patient is moved and/or the supply of the patient line is moved. In some embodiments, as shown in FIG. 7B, the first edge 38 and the second edge 44 are overlapped to further secure the channel 28.

FIG. 8 is a top view of one embodiment of the line manager 10 of the present invention in use. The line manager 10 is made of a flexible material to allow it to be secured to the bed rail such that the patient lines are positioned at or above the patient and in some instances at or above the top surface of the mattress. The line manager 10 includes a strap (not shown) extending from a proximal end 14 and a distal end 16 separated by a body portion 18. The strap (not shown) is flexible and can be wrapped or positioned about a surface or rod. The proximal end 14 includes one or more slots 20 and 22 although the embodiment in FIG. 8 depicts two slots 20 and 22, other embodiments may include 1, 2, 3, 4, 5, etc., slots. In addition, the proximal end 14 may include a snap or a loop-and-hook fastener or a combination thereof to secure the proximal end 14 and the distal end 16. The distal end 16 extends to a length sufficient to encircle an object that is to be secured, and as such the length may vary between embodiments. The distal end 16 may optionally have one or more ridges 24a-24i extending from the surface of the distal end 16. The width of the distal end 16 is sized as to frictionally fit through the one or more slots 20 and 22. In embodiments with one or more ridges 24a-24i extending from the surface of the distal end 16, the one or more ridges 24a-24i contact the one or more slots 20 and 22 to frictionally secure the proximal end 14 and the distal end 16 about the object (not shown). The distal end 16 may extend through the slot 20 and contact the divider 26 and further extend through the slot 22 such that the one or more ridges 24a-24i contact the divider 26 and secures the line manager 10. The body portion 18 includes a channel 28 formed by a first tab 30 and a second tab 32. The first tab 30 includes a first proximal edge 34 and a first distal edge 36 separated by a first edge 38. Adjacent the first tab 30 is a second tab 32 that includes a second proximal edge 40 and a second distal edge 42 separated by a second edge 44. A channel aperture 46 is formed between the first edge 38 and the second edge 44. In some instances, the first edge 38 and the second edge 44 are overlapped to further secure the channel 28. In this figure, two patient lines are depicted simultaneously positioned within the channel 28, however, the skilled artisan will understand that 2, 3, 4, 5, 6, 7, 8, 9, or more patient lines may be simultaneously held within the channel 28. Given that the patient lines are not firmly affixed within the channel (the lines do not encompass the entire area within the channel 28) the patient lines are retained without longitudinally restraining one or more patient care lines between the first curved flexible tab, the adjacent second curved flexible tab and the bottom of the channel. In other words, the one more patient lines (as depicted) are able to slide along the longitudinal axis of the patient line, but are removably restrained within the channel. Thus, the patient line is capable of being moved along its longitudinal axis to accommodate a repositioning of the patient line, e.g., when a patient is moved and/or the supply of the patient line is moved, without the patient line leaving the channel 28, thus providing for control of the location of the one or more patient lines around the bed, post, or other area around a patient, thus eliminating the tangling of the patient lines.

This is particularly helpful for staff when they are trying to prevent kinking or tangling of fluid lines in which fluid flow would be reduced or completely compromised.

Figure 9:
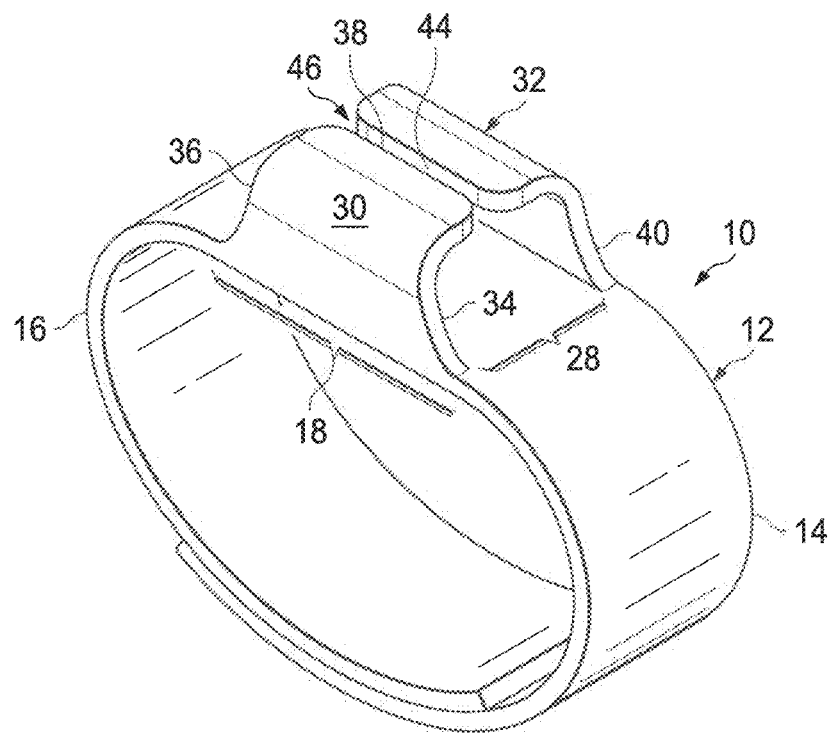
FIG. 9 is a perspective view of the line manager of the present invention.

FIG. 9 is a perspective view of the line manager 10 of the present invention. The line manager 10 is made of a flexible material to allow it to be secured to the bed rail such that the patient lines are positioned at or above the patient and in some instances at or above the top surface of the mattress. The line manager 10 includes a strap 12 extending from a proximal end 14 and a distal end 16 separated by a body portion 18. The strap 12 is flexible and can be wrapped or positioned about a surface or rod. In addition, the proximal end 14 may include a snap or a loop-and-hook fastener or a combination thereof to secure the proximal end 14 and the distal end 16. The distal end 16 extends to a length sufficient to encircle an object that is to be secured, and as such the length may vary between embodiments. The distal end 16 may optionally have a loop-and-hook fastener extending from the surface of the distal end 16 to frictionally secure the proximal end 14 and the distal end 16 about the object (not shown). The body portion 18 includes a channel 28 formed by a first tab 30 and a second tab 32. The first tab 30 includes a first proximal edge 34 and a first distal edge 36 separated by a first edge 38. Adjacent the first tab 30 is a second tab 32 that includes a second proximal edge 40 and a second distal edge (not shown) separated by a second edge 44. A channel aperture 46 is formed between the first edge 38 and the second edge 44. In some instances, the first edge 38 and the second edge 44 are overlapped to further secure the channel 28.

Figure 10A:
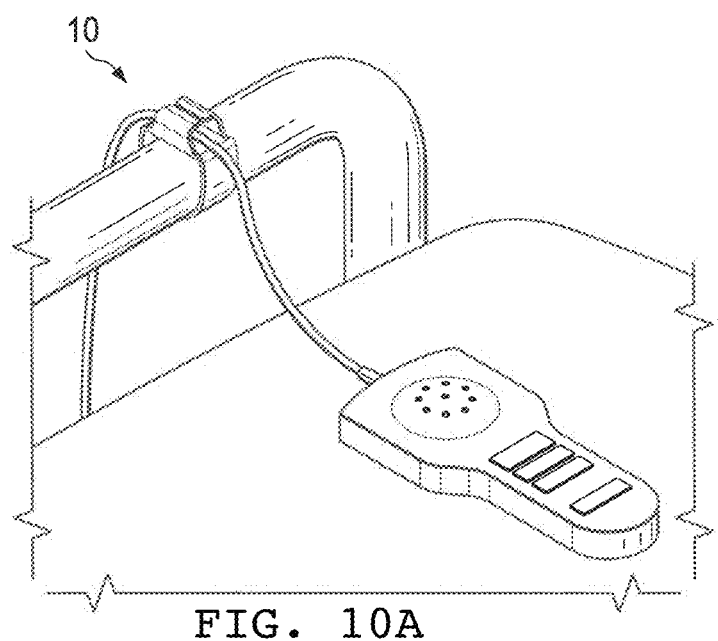
FIGS. 10A, 10B, 10C, and 10D are views of one embodiment of the line manager of the present invention in use.
Figure 10B:
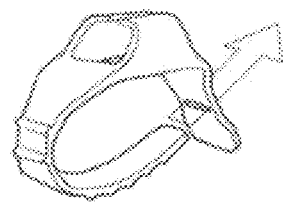
Figure 10C:
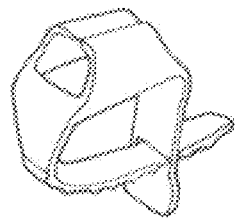
Figure 10D:
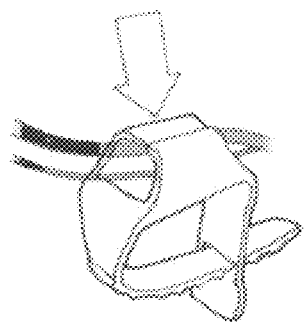
Figure 10E:
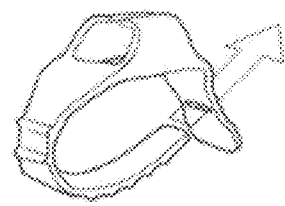
FIGS. 10E, 10F, and 10G, are views of one embodiment of the line manager of the present invention in use.
Figure 10F:
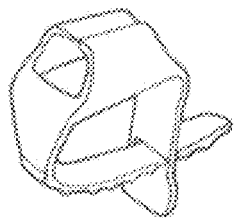
Figure 10G:
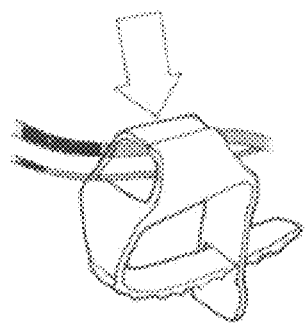

FIG. 10A is a view of one embodiment of the line manager 10 in use. FIG. 10B is an image of the line manager in operation where the line manager is placed around bedrail or stable fixture (not shown) and the notched end is inserted into upper thin slot on opposite end. FIG. 10C is an image of the line manager in use where the strap is pulled through until tight to lock line manager in place. The lower slot is fed through to direct the end down and out of the way. FIG. 10D is an image of the line manager in use where the feed tubes, cables, and cords are placed through the large clasp on top for organization, accessibility, and safety. FIG. 10E is an image of the line manager 10 in operation where the line manager 10 is placed around bedrail or stable fixture (not shown) and the notched end is inserted into the single slot 22 on the opposite end. FIG. 10F is an image of the line manager 10 in use where the strap is pulled through the single slot 22 until tight to lock line manager 10 in place. FIG. 10G is an image of the line manager 10 with the single slot 22 in use where the feed tubes, cables, and cords are placed through the large clasp on top for organization, accessibility, and safety.

In one embodiment, the present invention includes a line management device for attaching to a fixture that retains one or more patient care lines, wherein the device comprises, consists essentially of, or consists of: a flexible strap comprising a proximal strap end comprising a single slot positioned through a portion of the proximal strap end; a body portion connected to the proximal strap end, wherein the body portion comprises: a channel positioned on top of the flexible strap: wherein the channel is formed by (a) a bottom located under the one or more patient care lines, wherein the bottom is formed from the body portion, (b) a first curved flexible tab that extends from the body portion and curves towards (c) an adjacent second curved flexible tab that extends from the body portion and curves towards the first curved flexible tab, wherein the bottom and the first curved flexible tab and the adjacent second curved flexible tab form an opening that accommodates one or more patient care lines, wherein the opening is sized to allow the one or more patient care lines to be placed within the opening and the opening retains the one or more patient care lines without longitudinally restraining the one or more patient care lines or contacting the first curved flexible tab and the adjacent second curved flexible tab; and a distal strap end connected to the body portion, wherein the distal strap end extends through the single slot to secure the distal strap end to the proximal strap end. In one aspect, the flexible strap is rubber, polymer, plastic, or combinations thereof. In another aspect, the channel is parallel to the proximal strap end. In another aspect, the channel is perpendicular to the proximal strap end. In another aspect, the first curved flexible tab and the adjacent second curved tab flexible overlap. In another aspect, the opening does not restrain the one or more patient care lines.

In another embodiment, the present invention includes a line management device for removably simultaneously retaining one or more patient care lines comprising, consisting essentially of, or consisting of: a flexible strap comprising a proximal strap end that comprises a securing mechanism; a body portion connected to the proximal strap end, wherein the body portion comprises: a channel positioned on top of the flexible strap wherein the channel is formed by (a) a bottom located under the one or more patient care lines, wherein the bottom is formed from the body portion, (b) a first curved flexible tab that extends from the body portion and curves towards (c) an adjacent second curved flexible tab that extends from the body portion and curves towards the first curved flexible tab, wherein the first curved flexible tab and the adjacent second curved flexible tab overlap or form an opening wherein the opening is sized to allow the one or more patient care lines to be simultaneously placed within the opening and the opening simultaneously retains the one or more patient care lines without longitudinally restraining or contacting the first curved flexible tab and the adjacent second curved flexible tab the one or more patient care lines; and a distal strap end connected to the body portion, wherein the distal strap end comprises a connection mechanism that engages the securing mechanism of the proximal strap end to removably secure the proximal strap end to the distal strap end. In one aspect, the channel is parallel to the proximal strap end. In another aspect, the channel is perpendicular to the proximal strap end. In another aspect, the first curved tab and the adjacent second curved tab overlap. In another aspect, the securing mechanism comprises a hook closure and the connection mechanism comprises a loop closure to mate the securing mechanism and the connection mechanism. In another aspect, the securing mechanism and the connection mechanism comprise: a hook closure to mate the securing mechanism and the connection mechanism; a tab closure and the connection mechanism comprises an aperture closure to mate the securing mechanism and the connection mechanism; an aperture closure at the proximal strap end and the connection mechanism comprises a tab closure at the distal strap end to mate the securing mechanism and the connection mechanism; a single slot at the distal strap end and the connection mechanism comprises a tab at the proximal strap end, wherein the tab extends through the single slot to secure the securing mechanism and the connection mechanism; or a tab at the proximal strap end and the connection mechanism comprises a single slot at the distal strap end, wherein the tab extends through the single slot to secure the securing mechanism and the connection mechanism. In another aspect, the tab comprises one or more ridges to fit the securing mechanism and the connection mechanism.

In another embodiment, the present invention includes a method for retaining one or more patient care lines with a line management device comprising, consisting essentially of, or consisting of, the steps of: providing a flexible strap comprising a proximal strap end comprising a single slot positioned through a portion of the proximal strap end that comprises: a body portion connected to the proximal strap end, wherein the body portion comprises: a channel positioned on top of the flexible strap, wherein the channel is formed by (a) a bottom located under the one or more patient care lines, wherein the bottom is formed from the body portion, (b) a first curved flexible tab that extends from the body portion and curves towards (c) an adjacent second curved flexible tab that extends from the body portion and curves towards the first curved flexible tab, wherein the bottom and the first curved flexible tab and the adjacent second curved flexible tab form an opening that accommodates one or more patient care lines, wherein the opening is sized to allow the one or more patient care lines to be placed within the opening and the opening retains, but does not longitudinally restraining or contacting the first curved flexible tab or the adjacent second curved flexible tab, or both, the one or more patient care lines; and a distal strap end connected to the body portion, wherein the distal strap end extends through the single slot to secure the distal strap end to the proximal strap end; and attaching the device to a fixture, wherein one or more patient care lines can be placed and removed from the opening. In one aspect, the flexible strap is rubber, polymer, plastic, or combinations thereof. In another aspect, the channel is parallel to the proximal strap end. In another aspect, the channel is perpendicular to the proximal strap end. In another aspect, the first curved tab and the adjacent second curved tab overlap. In another aspect, the opening does not restrain the one or more patient care lines.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited features, elements, components, groups, integers, and/or steps, but do not exclude the presence of other unstated features, elements, components, groups, integers and/or steps. In embodiments of any of the compositions and methods provided herein, "comprising" may be replaced with "consisting essentially of" or "consisting of". As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only. As used herein, the phrase "consisting essentially of" requires the specified features, elements, components, groups, integers, and/or steps, but do not exclude the presence of other unstated features, elements, components, groups, integers and/or steps as well as those that do not materially affect the basic and novel characteristic(s) and/or function of the claimed invention.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

What is claimed is:

1. A line management device for attaching to a fixture that retains one or more patient care lines, wherein the device comprises:
    a flexible strap consisting of:
    a proximal strap end comprising a single slot positioned through a portion of the proximal strap end;
    a body portion of the flexible strap connected to the proximal strap end, wherein the body portion comprises: a channel positioned on top of the flexible strap, wherein the channel is formed by (a) a bottom located under the one or more patient care lines, wherein the bottom is formed from the body portion, (b) a first curved flexible tab that extends from the body portion and curves towards (c) an adjacent second curved flexible tab that extends from the body portion and curves towards the first curved flexible tab, wherein the bottom and the first curved flexible tab and the adjacent second curved flexible tab form an opening that accommodates one or more patient care lines, wherein the opening is sized to allow the one or more patient care lines to be placed within the opening and the opening retains the one or more patient care lines without longitudinally restraining the one or more patient care lines or contacting the first curved flexible tab and the adjacent second curved flexible tab; and
    a distal strap end connected to the body portion, wherein the distal strap end extends through the single slot to secure the distal strap end to the proximal strap end.

2. The line management device of claim 1, wherein the flexible strap is rubber, polymer, plastic, or combinations thereof.

3. The line management device of claim 1, wherein the channel is parallel to the proximal strap end.

4. The line management device of claim 1, wherein the channel is perpendicular to the proximal strap end.

5. The line management device of claim 1, wherein the first curved flexible tab and the adjacent second curved tab flexible overlap.

6. The line management device of claim 1, wherein the opening does not restrain the one or more patient care lines.

7. A line management device for removably simultaneously retaining one or more patient care lines comprising:
    a flexible strap consisting of:
    a proximal strap end that comprises a securing mechanism;
    a body portion of the flexible strap connected to the proximal strap end, wherein the body portion comprises: a channel positioned on top of the flexible strap wherein the channel is formed by (a) a bottom located under the one or more patient care lines, wherein the bottom is formed from the body portion, (b) a first curved flexible tab that extends from the body portion and curves towards (c) an adjacent second curved flexible tab that extends from the body portion and curves towards the first curved flexible tab, wherein the first curved flexible tab and the adjacent second curved flexible tab overlap to form an opening wherein the opening is sized to allow the one or more patient care lines to be simultaneously placed within the opening and the opening simultaneously retains the one or more patient care lines without longitudinally restraining or contacting the first curved flexible tab and the adjacent second curved flexible tab; and
    a distal strap end connected to the body portion, wherein the distal strap end comprises a connection mechanism that engages the securing mechanism of the proximal strap end to removably secure the proximal strap end to the distal strap end.

8. The line management device of claim 7, wherein the channel is parallel to the proximal strap end.

9. The line management device of claim 7, wherein the channel is perpendicular to the proximal strap end.

10. The line management device of claim 7, wherein the first curved tab and the adjacent second curved tab overlap.

11. A method for retaining one or more patient care lines with a line management device comprising the steps of:
    providing a flexible strap consisting of:
    a proximal strap end comprising a single slot positioned through a portion of the proximal strap end, a body portion of the flexible strap connected to the proximal strap end, wherein the body portion comprises: a channel positioned on top of the flexible strap, wherein the channel is formed by (a) a bottom located under the one or more patient care lines, wherein the bottom is formed from the body portion, (b) a first curved flexible tab that extends from the body portion and curves towards (c) an adjacent second curved flexible tab that extends from the body portion and curves towards the first curved flexible tab, wherein the bottom and the first curved flexible tab and the adjacent second curved flexible tab form an opening that accommodates one or more patient care lines, wherein the opening is sized to allow the one or more patient care lines to be placed within the opening and the opening retains, but without longitudinally restraining or contacting the first curved flexible tab or the adjacent second curved flexible tab, or both, the one or more patient care lines, and a distal strap end connected to the body portion, wherein the distal strap end extends through the single slot to secure the distal strap end to the proximal strap end; and
    attaching the device to a fixture, wherein one or more patient care lines can be placed and removed from the opening.

12. The method of claim 11, wherein the flexible strap is rubber, polymer, plastic, or combinations thereof.

13. The method of claim 11, wherein the channel is parallel to the proximal strap end.

14. The method of claim 11, wherein the channel is perpendicular to the proximal strap end.

15. The method of claim 11, wherein the first curved tab and the adjacent second curved tab overlap.

16. The method of claim 11, wherein the opening does not restrain the one or more patient care lines.

* * * * *